(12) United States Patent
Holloman et al.

(10) Patent No.: US 10,335,160 B1
(45) Date of Patent: Jul. 2, 2019

(54) TOURNIQUET BELT

(71) Applicant: Ballistipax, LLC, Melbourne, FL (US)

(72) Inventors: Jason Holloman, Cocoa, FL (US); David Malis, Melbourne, FL (US)

(73) Assignee: Ballistipax, LLC, Melbourne, FL (US)

( * ) Notice: Subject to any disclaimer, the term of this patent is extended or adjusted under 35 U.S.C. 154(b) by 0 days.

(21) Appl. No.: 16/292,401

(22) Filed: Mar. 5, 2019

(51) Int. Cl.
*A61B 17/132* (2006.01)

(52) U.S. Cl.
CPC ................................ *A61B 17/1322* (2013.01)

(58) Field of Classification Search
CPC .......................... A61B 17/1322; A61B 17/1327
See application file for complete search history.

(56) References Cited

U.S. PATENT DOCUMENTS

| | | | |
|---|---|---|---|
| 7,981,135 B2 | 7/2011 | Thorpe | |
| 8,343,182 B2 | 1/2013 | Kirkham | |
| 8,465,514 B1 | 6/2013 | Rose | |
| 8,707,468 B2 | 4/2014 | Reynolds et al. | |
| 9,730,703 B2 | 8/2017 | Rose et al. | |
| 9,730,704 B2 | 8/2017 | Rose et al. | |
| 9,750,507 B2 | 9/2017 | Brub | |
| 2003/0028215 A1* | 2/2003 | Brooks | A61B 17/1327 606/203 |
| 2005/0240217 A1* | 10/2005 | Jennifer | A61B 17/1322 606/203 |
| 2007/0032818 A1* | 2/2007 | McEwen | A61B 17/1322 606/202 |
| 2008/0183207 A1* | 7/2008 | Horne | A61B 17/1325 606/203 |
| 2009/0062843 A1* | 3/2009 | Heston | A61B 17/135 606/203 |
| 2011/0284322 A1 | 11/2011 | West | |
| 2012/0158041 A1 | 6/2012 | Craig | |
| 2012/0215254 A1* | 8/2012 | Brub | A61B 17/1327 606/203 |
| 2014/0090140 A1 | 4/2014 | Craig et al. | |
| 2015/0359542 A1 | 12/2015 | Steinbaugh et al. | |
| 2016/0345981 A1* | 12/2016 | Demas | A61B 17/1322 |
| 2017/0049459 A1 | 2/2017 | Harmon et al. | |
| 2018/0228497 A1 | 8/2018 | Dimino et al. | |
| 2018/0256172 A1 | 9/2018 | Black | |

* cited by examiner

*Primary Examiner* — Alexander J Orkin
(74) *Attorney, Agent, or Firm* — Kelly G. Swartz; Widerman Malek, PL

(57) ABSTRACT

A tourniquet belt including a first, second, third, fourth, and fifth elongate fabric member, belt fastener, and windlass. The second elongate fabric member having a stiffness greater than the stiffness of the first elongate fabric member and affixed to the first elongated fabric member along a tourniquet portion. The third elongate fabric member secured to the first elongate fabric forming a first pocket with an opening proximate the tourniquet portion. The fourth elongate fabric member secured to the first elongate fabric member forming a second pocket having an opening proximate the tourniquet portion. The fifth elongate fabric member carried within the first pocket, extending through the first and second pocket openings, across the tourniquet portion, and carried within the second pocket. The belt fastener secured to the first end of the first elongate fabric member. The windlass carried by the fifth elongate fabric member along the tourniquet portion.

20 Claims, 5 Drawing Sheets

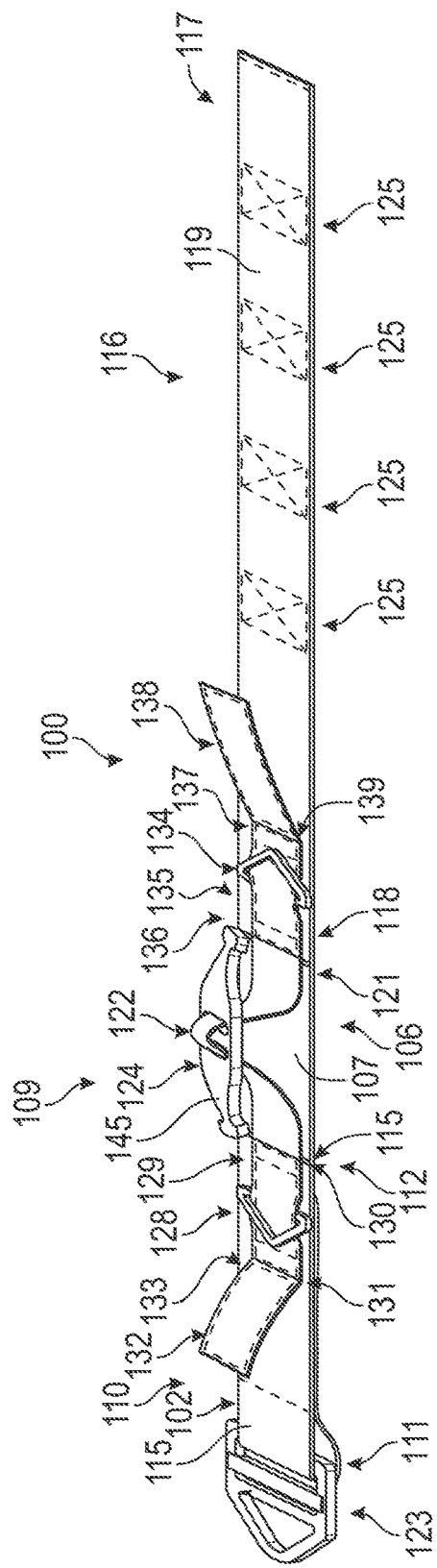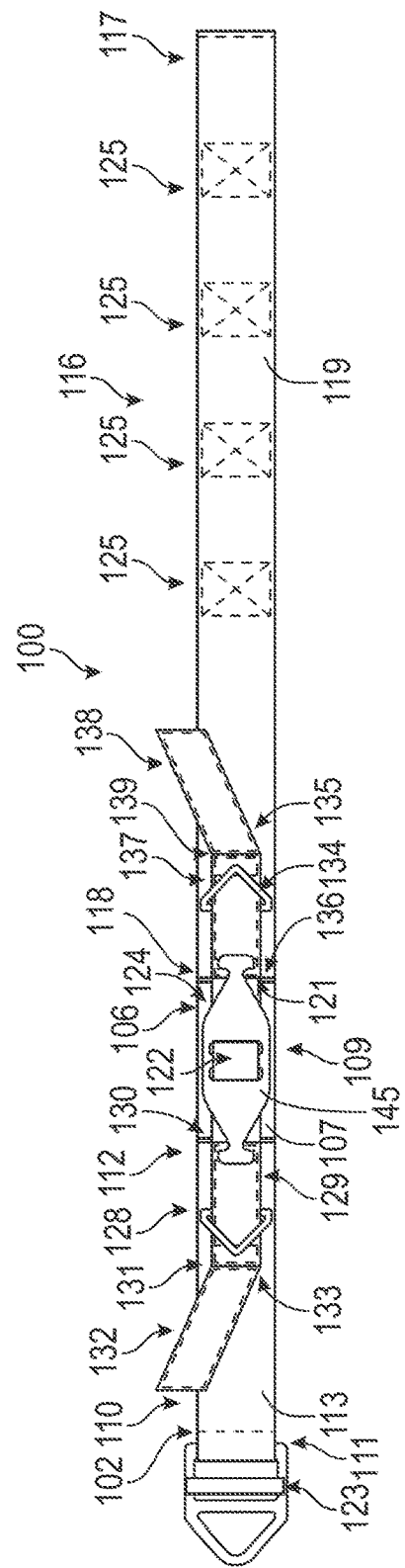

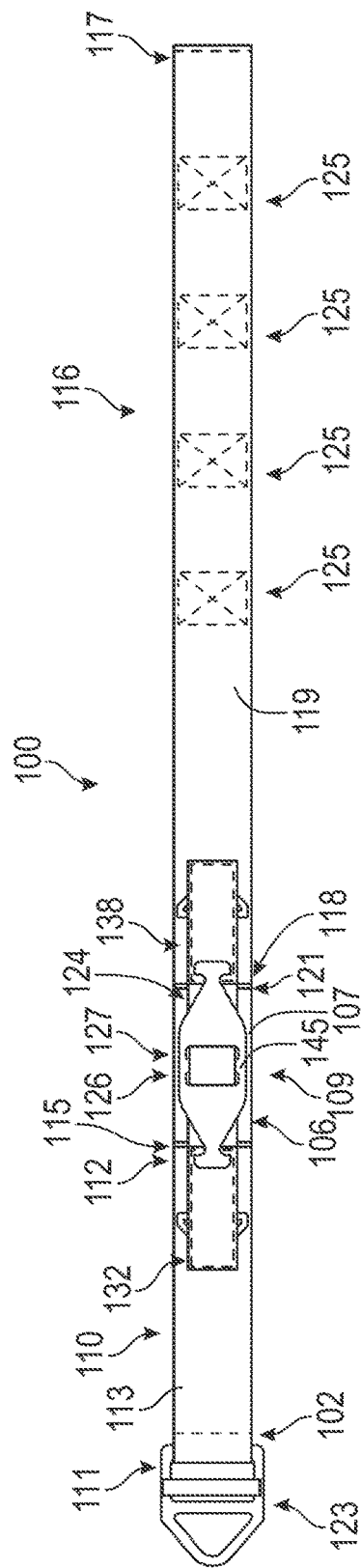
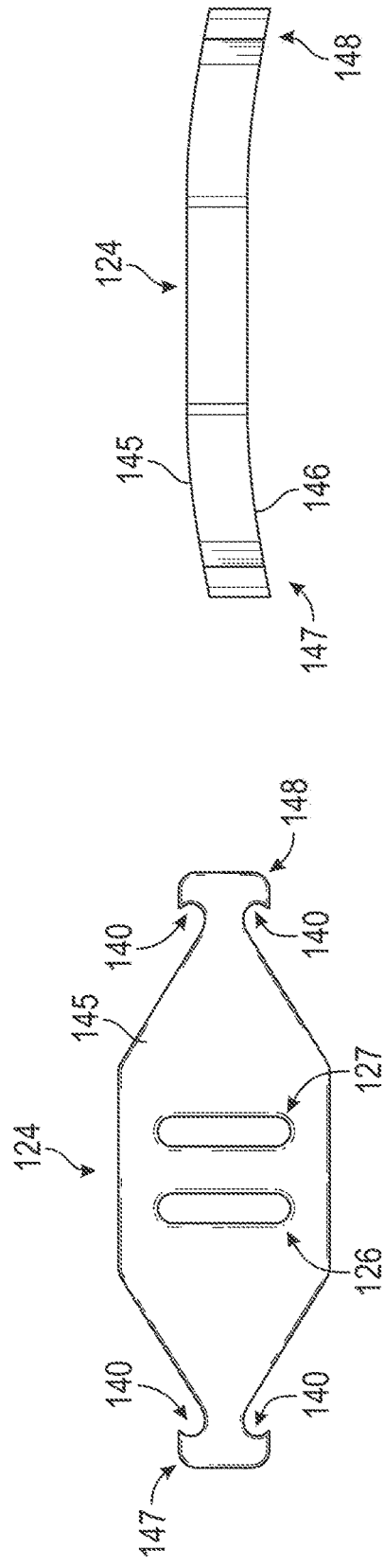

TOURNIQUET BELT

FIELD OF THE INVENTION

The present invention relates to systems and methods for medical devices used in first aid. More specifically, this invention relates to a tourniquet that can easily be worn as a belt when not in use.

BACKGROUND OF THE INVENTION

Tourniquets are used primarily to achieve occlusion of arterial blood flow. A typical tourniquet is a tightly tied band applied around a body part (an arm or a leg) in an attempt to stop severe bleeding or uncontrolled hemorrhage in an emergency situation. Tourniquets frequently found in the prior art consist of tightly tied bands that are applied around a body part such as an arm or a leg to stem the flow of blood. In one example of the application of a tourniquet, a piece of rubber tubing is wrapped around the limb and tied tightly. A stick is wound underneath the tubing and twisted until the tubing is tightened so that the bleeding is stopped. Once an adequate pressure on the limb is achieved, the stick is secured into its position.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

With the above in mind, embodiments of the present invention are related to a tourniquet belt including a first elongate fabric member, a second elongate fabric member, a third elongate fabric member, a fourth elongate fabric member, a fifth elongate fabric member, a belt fastener, and a windlass. The first elongate fabric member may have a first stiffness, a length, a first side, an opposing second side, a first end, and an opposing second end. The second elongate fabric member may have a first side, an opposing second side, a second stiffness greater than the first stiffness, and be affixed to the first elongated fabric member with the second side of the second elongate fabric member proximate the first side of the first elongate fabric member. An area of the second elongate fabric member, which overlays the first elongate fabric member, may define a tourniquet portion of the first elongate fabric member. The third elongate fabric member may have a length, a first side, an opposing second side, a first end, and an opposing second end. The third elongate fabric member may be secured to the first elongate fabric member with the second side of the third elongate fabric member proximate the first side of the first elongate fabric member and a second end of the third elongate fabric member proximate the tourniquet portion. The first end of the third elongate fabric member may extend distal the tourniquet portion and secure to the first elongate fabric member along the lengths of the third elongate fabric member, the first elongate fabric member, and the first end of the third elongate fabric member to form a first pocket having a first pocket opening proximate the tourniquet portion of the first elongate fabric member. The fourth elongate fabric member may have a length, a first side, an opposing second side, a first end, and an opposing second end. The fourth elongate fabric member may be secured to the first elongate fabric member with the second side of the fourth elongate fabric member proximate the first side of the first elongate fabric member and a second end of the fourth elongate fabric member proximate the tourniquet portion. The first end of the fourth elongate fabric member may extend distal the tourniquet portion and secure to the first elongate fabric member along the lengths of the fourth elongate fabric member, the first elongate fabric member, and the first end of the fourth elongate fabric member to form a second pocket having a second pocket opening proximate the tourniquet portion of the first elongate fabric member. The fifth elongate fabric member may be carried within the first pocket, extend through the first pocket opening, across the tourniquet portion, through the second pocket opening, and be carried within the second pocket. The belt fastener may be secured to the first end of the first elongate fabric member. The windlass may be carried by the fifth elongate fabric member along the tourniquet portion.

The belt fastener may include an adjustable slide buckle.

The tourniquet belt may include a plurality of attachment points at which the fifth elongate fabric member is secured to the fourth elongate fabric member and first elongate fabric member.

The windlass may include a first and second aperture. The first aperture may be adapted to receive the fifth elongate fabric member. The second aperture may be adapted to receive the fifth elongate fabric member.

A surface of the windlass, proximate the first surface of the second elongate fabric member, may be arcuate.

The tourniquet belt may include a first retaining member secured to the third elongate fabric member and adapted to capture a first end of the windlass.

The tourniquet belt may include a first securing fabric member having a first end secured to the third elongate fabric member proximate the tourniquet portion and an opposing second end secured to the third elongate fabric member with the first retaining member carried on the first securing fabric member between the first and second end of the first securing fabric.

The tourniquet belt may include a first covering fabric member having a first end secured to the second end of the first securing fabric. A length of the first covering fabric may be adapted to removably secure to a length of the first securing fabric capturing the first retaining member therebetween.

The tourniquet belt may include a second retaining member secured to the fourth elongate fabric member and adapted to capture a second end of the windlass.

The tourniquet belt may include a second securing fabric member having a first end secured to the fourth elongate fabric member proximate the tourniquet portion and an opposing second end secured to the fourth elongate fabric member with the second retaining member carried on the second securing fabric member between the first and second end of the second securing fabric.

The tourniquet belt may include a second covering fabric member having a first end secured to the second end of the second securing fabric. A length of the second covering fabric may be adapted to removably secure to a length of the second securing fabric capturing the second retaining member therebetween.

The windlass may include a retaining notch on a first end of the windlass. The retaining notch may be adapted to receive a portion of at least one retaining member. An edge defining the retaining notch may be tapered.

The retaining member may be adjustably secured to the third elongate fabric member and positionable to change a distance between the retaining member and the windlass.

At least a first end of the windlass may be carried in the first pocket. A second end of the windlass may be carried in the second pocket.

A distance between a first hem of the third elongate fabric member and a first hem of the fourth elongate fabric member may be greater than a length of the windlass.

A ratio of a length of the windlass to a distance between the first pocket opening and the second pocket opening may be 1.3.

BRIEF DESCRIPTION OF THE DRAWINGS

FIG. 1 is a top perspective view of a tourniquet belt in a deployed configuration according to an embodiment of the present invention.

FIG. 2 is a top plan view of the tourniquet belt of FIG. 1 in a retainer released configuration.

FIG. 3 is a top plan view of the tourniquet belt of FIG. 1 in a compact configuration.

FIG. 4 is a top plan view of a windlass of the tourniquet belt of FIG. 1.

FIG. 5 is a side elevation view of the windlass of FIG. 4.

DETAILED DESCRIPTION OF THE INVENTION

Figure 6:
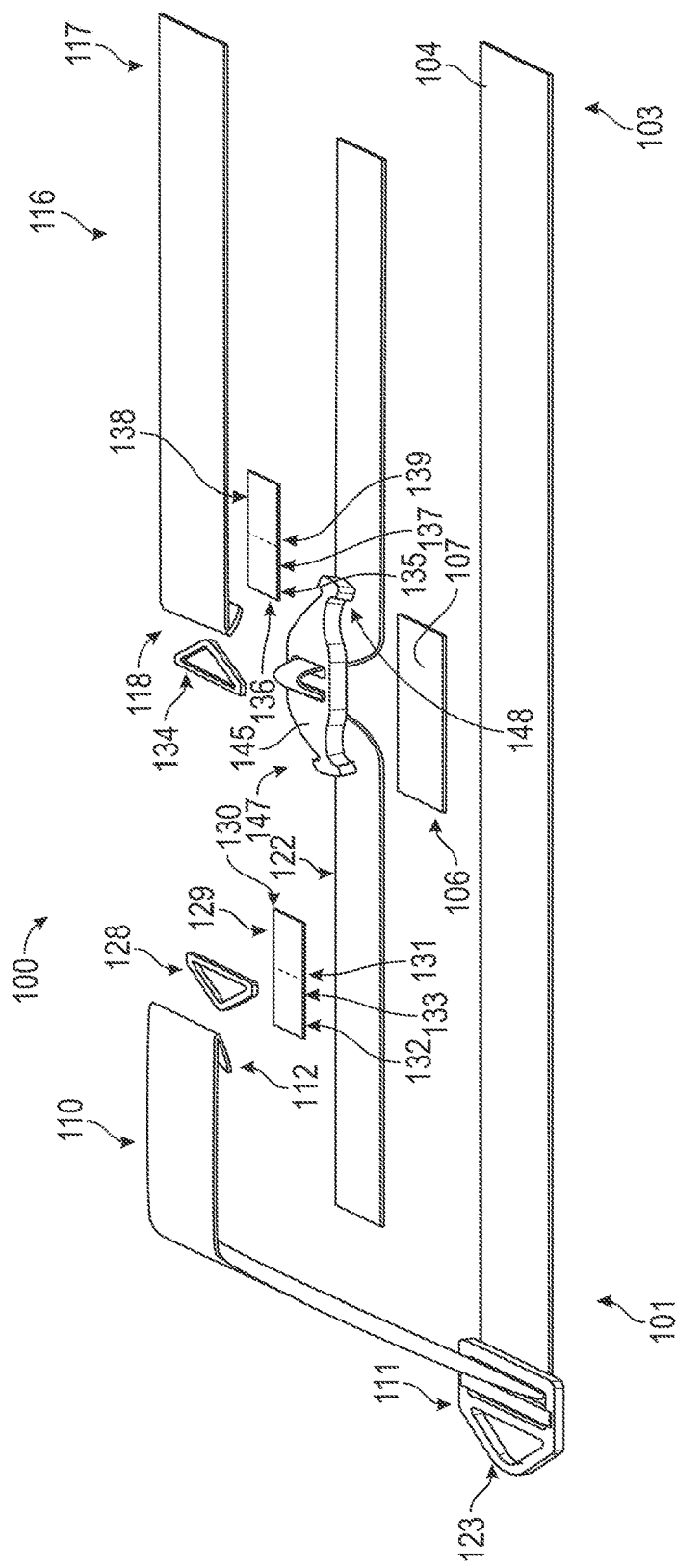
FIG. 6 is a side exploded view of the tourniquet belt of FIG. 1.
Figure 7:
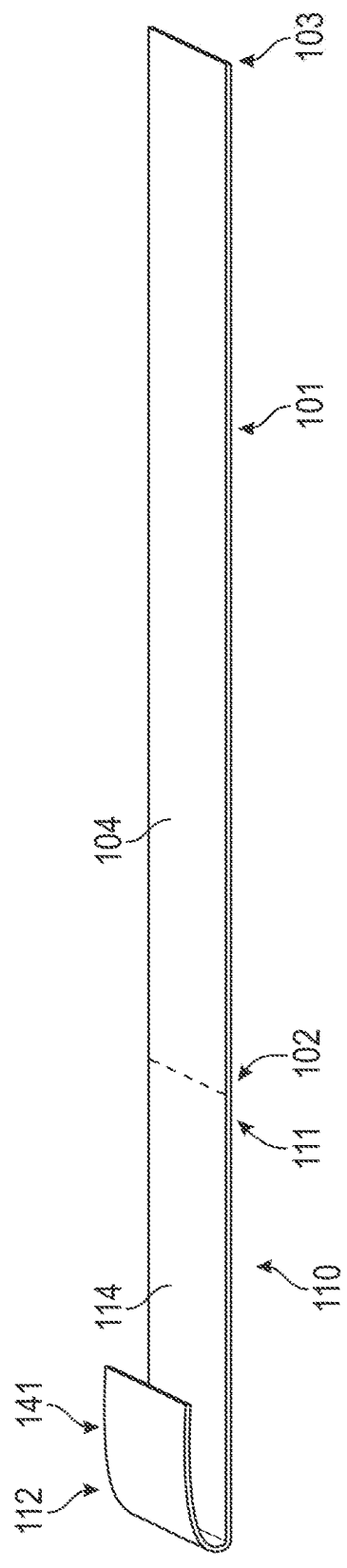
FIG. 7 is a top perspective view of the first and third elongate fabric members of the tourniquet belt of FIG. 1.
Figure 8:
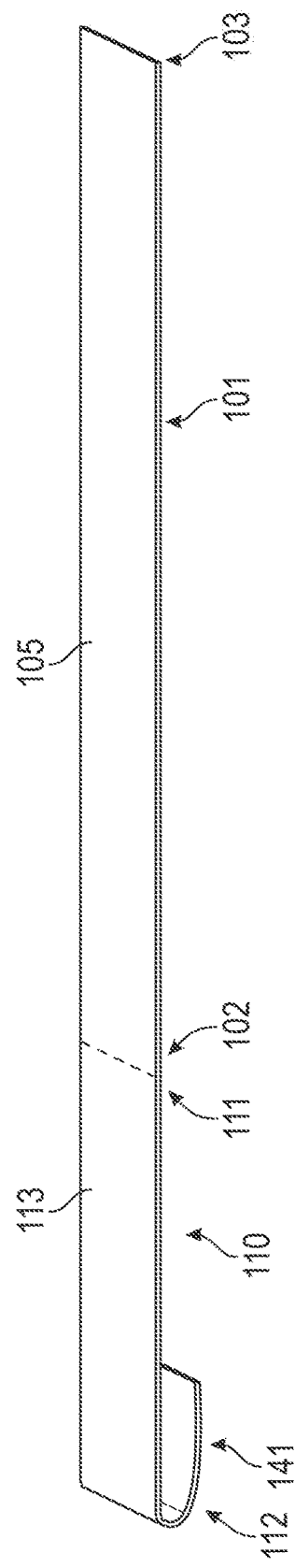
FIG. 8 is a bottom perspective view of the first and third elongate fabric members of FIG. 7.
Figure 9:
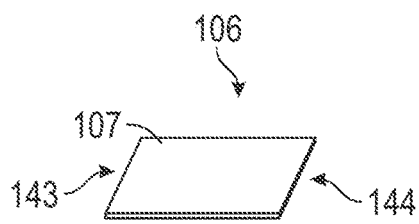
FIG. 9 is a top perspective view of the second elongate fabric member of the tourniquet belt of FIG. 1.
Figure 10:
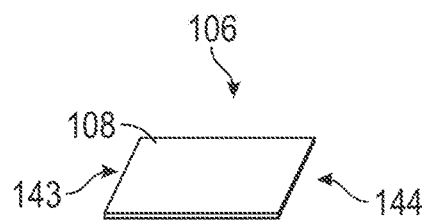
FIG. 10 is a bottom perspective view of the second elongate fabric member of FIG. 9.
Figure 11:
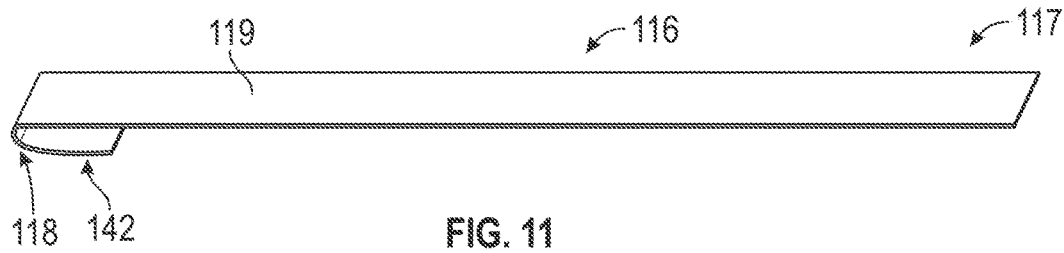
FIG. 11 is a top perspective view of the fourth elongate fabric member of the tourniquet belt of FIG. 1.
Figure 12:
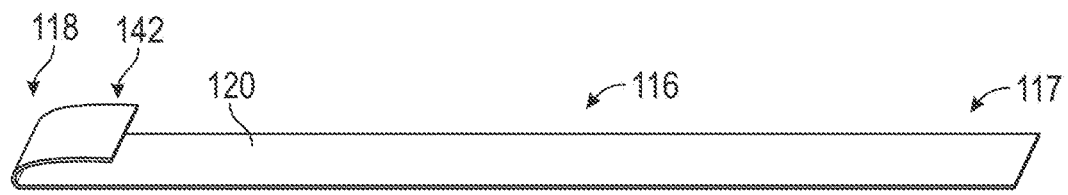
FIG. 12 is a bottom perspective view of the fourth elongate fabric member of FIG. 11.
Figure 13:
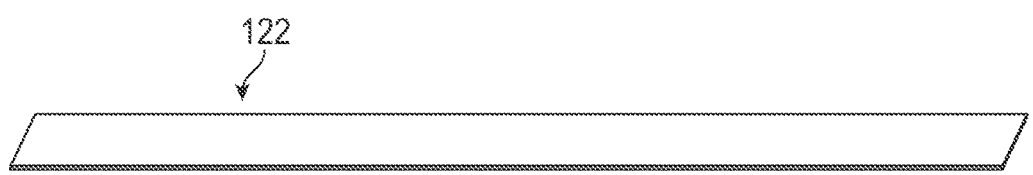
FIG. 13 is a top perspective view of the fifth elongate fabric member of the tourniquet belt of FIG. 1.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

An embodiment of the invention, as shown and described by the various figures and accompanying text, provides a tourniquet belt 100. The tourniquet belt 100 may be adapted to be worn with conventional pants or shorts. When the need for application of the tourniquet belt 100 arises, the wearer may remove the tourniquet belt 100 from his or her waist and secure it around the affected body part. The belt fastener 123 may secure a first end 102 and an opposing second end 103 of the belt to one another in an adjustable manner. The belt fastener 123 may be adjusted to alter the circumference of the tourniquet by moving the second end 103 of the belt through the belt fastener 123. After the tourniquet belt 100 is secured to the affected body part, the windlass 124 may be rotated to apply pressure to the affected body part and occlude arterial blood flow.

The tourniquet belt 100 may include five elongate fabric members 101, 106, 110, 116, and 122, a belt fastener 123, and a windlass 124. Each of the five elongate fabric members 101, 106, 110, 116, and 122 may include nylon webbing.

The first elongate fabric member 101 may extend essentially the entirety of the length of the tourniquet belt 100. The first elongate fabric member 101 may be positioned closest to the wearer's body when the tourniquet belt 100 is worn by a user with other components of the tourniquet belt 100 secured to a first side 104 of the first elongate fabric member 101 distal the wearer's body. The first elongate fabric member 101 may have a length with the first side 104 of the elongate fabric member 101 extending an entirety of that length and an opposing second side 105 also extending an entirety of the length. The first elongate fabric member 101 may have a stiffness, which allows it to flex. The second end 103 may be brought toward the first end 102 and captured by the belt fastener 123 to form a loop between the first end 102 and second end 103. A portion of the length may be moved through the belt fastener 123 to adjust the circumference of the loop as necessary. The circumference may be large when the tourniquet belt 100 is worn as a belt than when it is used as a tourniquet around a person's arm.

The second elongate fabric member 106 may be secured to the first elongate fabric member 101 with a second side 108 of the second elongate fabric member proximate the first side 104 of the first elongate fabric member 101 and an opposing, second side 108 of the second elongate fabric member 106. The second elongate fabric member 106 may have a stiffness greater than that of the first elongate fabric member 101, particularly along a longitudinal access. The stiffness of the second elongate fabric member 106 may reinforce the first elongate fabric member 101 and prevent the portion of the tourniquet belt 100 along which the second elongate fabric member 106 is secured from bunching when the tourniquet belt 100 is tightened to occlude arterial blood flow. The portion of the tourniquet belt 100 along which the second elongate fabric member 106 is placed may be referred to as the tourniquet portion 109. The tourniquet portion 109 may be defined as the portion of the tourniquet belt 100 between a first end 143 and an opposing second end 144 of the second elongate fabric member 106.

The third elongate fabric member 110 may have a second side 114, which is secured proximate a first side 104 of the first elongate fabric member 101, and an opposing first side 113. The third elongate fabric member 110 may also have a first end 111 and an opposing second end 112.

In one embodiment, the third elongate fabric member 110 may be monolithically formed with the first elongate fabric member 101. In such an embodiment, the first end 111 of the third elongate fabric 110 member may be defined as the portion of the tourniquet belt 100 which covers the outward facing portion of the belt fastener 123, while the first end 102 of the first elongate fabric member 101 may be defined as the portion of the tourniquet belt 100 which covers the inward facing portion of the belt fastener 123.

In another embodiment, the third elongate fabric member 110 may be secured to the first elongate fabric member 101 and the first elongate fabric member 101 and third elongate fabric member 116 may not be a monolithic unit.

A first pocket may be formed between the third elongate fabric member 110 and the first elongate fabric member 101. The pocket may be formed by securing at least a portion of the length of the third elongate fabric member 110 to a portion of the length of the first elongate fabric member 101. These lengths may be secured together by stitching along both a top and bottom edge of the lengths. Optionally, the first end 111, or a location proximate the first end 111, of the third elongate fabric member 110 may be secured proximate the first end 102 of the first elongate fabric member 101. In embodiments in which these ends 111 and 102 are secured together with stitching, a fifth elongate fabric member 122 may also be secured with stitching at this location.

The second end 112 of the third elongate fabric member 110 may be positioned proximate the tourniquet portion 109. A first pocket opening 115 may be formed between the third elongate fabric member 110 and the first elongate fabric member 101 at the second end 112 of the third elongate fabric member 110. The fifth elongate fabric member 122 may be secured within the first pocket and extend through the first pocket opening 115.

The third elongate fabric member 110 may have a hem 141 within the first pocket. In embodiments with a third elongate fabric member 110 hem 141 within the first pocket, the second end 112 of the third elongate fabric member 110 may be the portion of the third elongate fabric member 110 positioned closest to the tourniquet portion 109. The hem 141 may be formed by folding a portion of the third elongate fabric member 110 so a portion of the second side 114 is proximate the second side 114 along a portion of the length of the third elongate fabric member 110 which forms the first pocket.

The fourth elongate fabric member 116 may have a second side 120, which is secured proximate a first side 104 of the first elongate fabric member 101, and an opposing first side 119. The fourth elongate fabric member 116 may also have a first end 117 and an opposing second end 118.

In one embodiment, the fourth elongate fabric member 116 may be monolithically formed with the first elongate fabric member 101. In such an embodiment, the first end 117 of the fourth elongate fabric member 116 may be defined as the portion of the fourth elongate fabric member 116 most distal the belt fastener 123, while the second end 103 of the first elongate fabric member 101 may also be defined as the portion of the first elongate fabric member 101 most distal the belt fastener 123.

In another embodiment, the fourth elongate fabric member 116 may be secured to the first elongate fabric member 101 and the first elongate fabric member 101 and fourth elongate fabric member 116 may not be a monolithic unit.

A second pocket may be formed between the fourth elongate fabric member 116 and the first elongate fabric member 101. The pocket may be formed by securing at least a portion of the length of the fourth elongate fabric member 116 to a portion of the length of the first elongate fabric member 101. These lengths may be secured together by stitching along both a top and bottom edge of the lengths. Optionally, the first end 117, or a location proximate the first end 117, of the fourth elongate fabric member 116 may be secured proximate the second end 103 of the first elongate fabric member 101. In embodiments in which these ends 117 and 103 are secured together with stitching, a fifth elongate fabric member 122 may also be secured with stitching at this location.

The second end 118 of the fourth elongate fabric member 116 may be positioned proximate the tourniquet portion 109. A second pocket opening 121 may be formed between the fourth elongate fabric member 116 and the first elongate fabric member 101 at the second end 118 of the fourth elongate fabric member 116. The fifth elongate fabric member 122 may be secured within the second pocket and extend through the second pocket opening 121.

The fourth elongate fabric member 116 may have a hem 142 within the second pocket. In embodiments with a fourth elongate fabric member 116 hem 142 within the second pocket, the second end 118 of the fourth elongate fabric member 116 may be the portion of the fourth elongate fabric member 116 positioned closest to the tourniquet portion 109. The hem 142 may be formed by folding a portion of the fourth elongate fabric member 116 so a portion of the second side 120 is proximate the second side 120 along a portion of the length of the fourth elongate fabric member 116 which forms the second pocket.

The longest length between the hem 141 of the third elongate fabric member 110 and the hem 142 of the fourth elongate fabric member 116 may be greater than a length of the windlass 124. Such a configuration may prevent a first end 147 or second end 148 of the windlass 124 from snagging a hem 141, 142 when removed from the first pocket or second pocket.

A fifth elongate fabric member 122 may have a length extending essentially the length of the tourniquet belt 100. The fifth elongate fabric member 122 may be secured to the first elongate fabric member 101 or third elongate fabric member 110 proximate the belt fastener 123, be carried within the first pocket, extend through the first pocket opening 115, across the tourniquet portion 109, through the second pocket opening 121, and be carried within the second pocket. The fifth elongate fabric member 122 may also be secured to the first elongate fabric member 101 or fourth elongate fabric member 116 at a plurality of attachment points 125. Because of the plurality of attachment points 125, the length of the tourniquet belt 100 may be shortened by cutting the tourniquet belt 100 and the fifth elongate fabric member 122 will remain secured within the second pocket.

The windlass 124 may be a monolithic plastic component and may be adapted to be carried by the fifth elongate fabric member 122 and positioned in the tourniquet portion 109. The windlass 124 may have a plurality of apertures 126, 127 adapted to receive the fifth elongate fabric member 122. In one embodiment, the windlass 124 may have a second side 146 proximate the first side 107 of the second elongate fabric member 106 and an opposing, first side 145. The fifth elongate fabric member 122 may be positioned between the second elongate fabric member 106 and a second side 146 of the windlass 124. A first aperture 126 of the windlass 124 may receive the fifth elongate fabric member 122 as the fifth elongate fabric member 122 moves from the second side 146 of the windlass 124 to the first side 145 of the windlass 124. The fifth elongate fabric member 122 may be positioned proximate the first side 145 of the windlass 124 between the first aperture 126 and the second aperture 127. The second aperture 127 may receive the fifth elongate fabric member 122 as the fifth elongate fabric member 122 move from the first side 145 of the windlass 124 to the second side 146 of the windlass 124 between the windlass 124 and the second elongate fabric member 106.

The second side 146 of the windlass 124 may be arcuate wherein the surface of the second side 146 is concave. The first side 145 of the windlass 124 may be arcuate wherein the surface of the first side 145 is convex. The arcuate angle of the windlass 124 may be small and designed to allow the windlass 124 to be worn on a user's hip and curve with the contours of the user's hip.

The windlass 124 may have a first end 147 and an opposing second end 148. The first end 147 may be nominally positioned proximate the belt fastener 123 while the second end 148 may be nominally positioned distal the belt fastener 123. When the tourniquet belt 100 is worn as a belt around a user's waist and not in use as a tourniquet, the first end 147 of the windlass 124 may enter the first pocket opening 115 and be carried by the first pocket. Similarly, when the tourniquet belt 100 is worn as a belt around a user's waist and not in use as a tourniquet, the second end 148 of the windlass 124 may enter the second pocket opening 121 and be carried by the second pocket. The arcuate angle and the ratio between a windlass 124 length and a distance between the first pocket opening 115 and the second pocket opening 121 may be such that the first end 147 or second end 148 of the windlass is ejected by the first pocket or second pocket, respectively, when the tourniquet belt 100 is positioned in a loop sized to fit around a user's leg or arm. In one embodiment, the ratio of a length of the windlass 124 to a distance between the first pocket opening 115 and the second pocket opening 121 may range from 1.4-1.2. In one embodiment, the ratio may be 1.3.

In use, the tourniquet belt 100 may be secured around a bleeding body part and the windlass 124 may be rotated to twist the fifth elongate fabric member 122, thereby shortening the effective length of the fifth elongate fabric member 122. As the windlass 124 is rotated and the fifth elongate fabric member 122 twisted, the diameter of the loop formed by the tourniquet belt 100 may be reduced, which puts pressure on an artery and occludes arterial blood flow.

When in use as a tourniquet, the windlass 124 may be rotated to twist the fifth elongate fabric member 122, which may apply pressure to an artery. The force created by twisting the windlass 124, may operate to untwist the fifth elongate fabric member 122 unless a counterforce is maintained on the windlass 124. Because untwisting of the windlass 124 is undesirable and reduces the effectiveness of the windlass, a first retaining member 128 may be secured to the third elongate fabric member 110 and adapted to capture a first end 147 or second end 148 of the windlass 124. This first retaining member 128 may be configured to capture the first end 147 or second end 148 of the windlass 124 and prevent the fifth elongate fabric member 122 from untwisting and relieving pressure applied by the tourniquet belt 100. Similarly, a second retaining member 134 may be secured to the fourth elongate fabric member 116 and adapted to capture a first end 147 or second end 148 of the windlass 124. This second retaining member 134 may be configured to capture the first end 147 or second end 148 of the windlass 124 and prevent the fifth elongate fabric member 122 from untwisting and relieving pressure applied by the tourniquet belt 100. In one embodiment, the first retaining member 128 or second retaining member 134 may be a d-ring, triangle ring, or the like.

The first end 147 or second end 146 or the windlass may be configured to receive a portion of the retaining members 128, 134. As shown in FIG. 4, a retaining notch 140 may be formed along a first or second edge of the first end 147 or second end 146. The retaining notch 140 may have a profile corresponding to a profile of the retaining members 128 and 134. An outer portion of the retaining notch 140 may taper.

A first securing fabric member 129 may secure the first retaining member 128 to the third elongate fabric member 110. A first end 130 of the first securing fabric member 129 may be positioned and affixed to the third elongate fabric member 110 proximate the tourniquet portion 109 and an opposing, second end 131 of the first securing fabric member 129 may be secured to the third elongate fabric member 110 distal the tourniquet portion 109. The first retaining member 128 may be carried by the first securing fabric member 129 between its first end 130 and second end 132 and configured to adjustably slide along the length of the first retaining member 128 between the first end 130 and the second end 132. This configuration may allow the first retaining member 128 to positionably change a distance between the first retaining member 128 and the windlass 124. Such a positionability may be advantage because, when in use, the windlass 124 may shift off center of the tourniquet portion 109 and may not be securable by statically attached retaining members.

A first covering fabric member 132 may be removably secured to the first securing fabric member 129, capturing the first retaining member 128 therebetween. A first end 133 of the first covering fabric member 132 may be secured to the second end 131 of the first securing fabric member 129. In one embodiment, the first covering fabric member 132 may be monolithically formed with the first securing fabric member 129. A length of the first covering fabric member 132 may be adapted to secure to a length of the first securing fabric member 129 using hooks and loop fasteners or the like.

A second securing fabric member 135 may secure the second retaining member 134 to the fourth elongate fabric member 116. A first end 136 of the second securing fabric member 135 may be positioned and affixed to the fourth elongate fabric member 116 proximate the tourniquet portion 109 and an opposing, second end 137 of the second securing fabric member 135 may be secured to the fourth elongate fabric member 116 distal the tourniquet portion 109. The second retaining member 134 may be carried by the second securing fabric member 135 between its first end 136 and second end 137 and configured to adjustably slide along the length of the second retaining member 134 between the first end 136 and the second end 137. This configuration may allow the second retaining member 134 to positionably change a distance between the second retaining member 134 and the windlass 124. Such a positionability may be advantage because, when in use, the windlass 124 may shift off center of the tourniquet portion 109 and may not be securable by statically attached retaining members.

A second covering fabric member 138 may be removably secured to the second securing fabric member 135, capturing the second retaining member 134 therebetween. A first end 139 of the second covering fabric member 138 may be secured to the second end 137 of the second securing fabric member 135. In one embodiment, the second covering fabric member 138 may be monolithically formed with the second securing fabric member 135. A length of the second covering fabric member 138 may be adapted to secure to a length of the second securing fabric member 135 using hooks and loop fasteners or the like.

A belt fastener 123 may be secured to the first end 102 of the first elongate fabric member 101 or a first end 111 of the third elongate fabric member 110. The belt fastener 123 may be adapted to capture the second end 103 of the first elongate fabric member 103 and form a loop of the first elongate fabric member 101. The circumference of the loop may be adjusted by positioning the length of the first elongate fabric member 101 within the belt fastener 123. Positioning a greater amount of the length of the first elongate fabric member 101 through the belt fastener 123 may reduce the circumference of the loop, while positioning a smaller amount of the length of the first elongate fabric member 101 through the belt fastener 123 may increase the circumference of the loop. In one embodiment, the belt fastener 123 may include a slide buckle, which may be adjustable.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Thus, the scope of the invention should be determined by the appended claims and their legal equivalents, and not by the examples given.

That which is claimed is:

1. A tourniquet belt comprising:
   a first elongate fabric member having a first stiffness, a length, a first side, an opposing second side, a first end, and an opposing second end;
   a second elongate fabric member having a first side, an opposing second side, a second stiffness greater than the first stiffness, and affixed to the first elongated fabric member with the second side of the second elongate fabric member proximate the first side of the first elongate fabric member, wherein an area of the second elongate fabric member, which overlays the first elongate fabric member, defines a tourniquet portion of the first elongate fabric member;
   a third elongate fabric member having a length, a first side, an opposing second side, a first end, and an opposing second end, wherein the third elongate fabric member is secured to the first elongate fabric member with the second side of the third elongate fabric member proximate the first side of the first elongate fabric member and a second end of the third elongate fabric member proximate the tourniquet portion, wherein the first end of the third elongate fabric member extends distal the tourniquet portion and secures to the first elongate fabric member along the lengths of the third elongate fabric member and the first elongate fabric member to form a first pocket having a first pocket opening proximate the tourniquet portion of the first elongate fabric member;
   a fourth elongate fabric member having a length, a first side, an opposing second side, a first end, and an opposing second end, wherein the fourth elongate fabric member is secured to the first elongate fabric member with the second side of the fourth elongate fabric member proximate the first side of the first elongate fabric member and a second end of the fourth elongate fabric member proximate the tourniquet portion, wherein the first end of the fourth elongate fabric member extends distal the tourniquet portion and secures to the first elongate fabric member along the lengths of the fourth elongate fabric member and the first elongate fabric member and the first end of the fourth elongate fabric member to form a second pocket having a second pocket opening proximate the tourniquet portion of the first elongate fabric member;
   a fifth elongate fabric member carried within the first pocket, extending through the first pocket opening, across the tourniquet portion, through the second pocket opening, and carried within the second pocket;
   a belt fastener secured to the first end of the first elongate fabric member, and
   a windlass carried by the fifth elongate fabric member along the tourniquet portion.

2. The tourniquet belt according to claim 1 wherein the belt fastener comprises an adjustable slide buckle.

3. The tourniquet belt according to claim 1 further comprising:
   a plurality of attachment points at which the fifth elongate fabric member is secured to the fourth elongate fabric member and first elongate fabric member.

4. The tourniquet belt according to claim 1 wherein the windlass comprises:
   a first aperture adapted to receive a portion of the fifth elongate fabric member; and
   a second aperture adapted to receive a portion of the fifth elongate fabric member.

5. The tourniquet belt according to claim 1 wherein a surface of the windlass is arcuate.

6. The tourniquet belt according to claim 1 further comprising:
a first retaining member secured to the third elongate fabric member and adapted to capture a first end or second end of the windlass.

7. The tourniquet belt according to claim 6 further comprising:
a first securing fabric member having a first end secured to the third elongate fabric member proximate the tourniquet portion and an opposing second end secured to the third elongate fabric member with the first retaining member carried on the first securing fabric member between the first and second end of the first securing fabric member.

8. The tourniquet belt according to claim 7 further comprising:
a first covering fabric member having a first end secured to the second end of the first securing fabric wherein a length of the first covering fabric member is adapted to removably secure to a length of the first securing fabric capturing the first retaining member therebetween.

9. The tourniquet belt according to claim 8 further comprising:
a second retaining member secured to the fourth elongate fabric member and adapted to capture a second end of the windlass.

10. The tourniquet belt according to claim 9 further comprising:
a second securing fabric member having a first end secured to the fourth elongate fabric member proximate the tourniquet portion and an opposing second end secured to the fourth elongate fabric member with the second retaining member carried on the second securing fabric member between the first and second end of the second securing fabric.

11. The tourniquet belt according to claim 10 further comprising:
a second covering fabric member having a first end secured to the second end of the second securing fabric wherein a length of the second covering fabric is adapted to removably secure to a length of the second securing fabric capturing the second retaining member therebetween.

12. The tourniquet belt according to claim 6 wherein the windlass comprises a retaining notch on the first end of the windlass, wherein the retaining notch is adapted to receive a portion of at least one retaining member.

13. The tourniquet belt according to claim 12 wherein an edge defining the retaining notch is tapered.

14. The tourniquet belt according to claim 6 wherein the retaining member is adjustably secured to the third elongate fabric member and positionable to change a distance between the retaining member and the windlass.

15. The tourniquet belt according to claim 1 wherein at least a first end of the windlass is carried in the first pocket.

16. The tourniquet belt according to claim 15 wherein a second end of the windlass is carried in the second pocket.

17. The tourniquet belt according to claim 1 wherein a distance between a first hem of the third elongate fabric member and a first hem of the fourth elongate fabric member is greater than a length of the windlass.

18. The tourniquet belt according to claim 1 wherein a ratio of a length of the windlass to a distance between the first pocket opening and the second pocket opening is between 1.4 and 1.2.

19. A tourniquet belt comprising:
a first elongate fabric member having a first stiffness, a length, a first side, an opposing second side, a first end, and an opposing second end;
a second elongate fabric member having a first side, an opposing second side, a second stiffness greater than the first stiffness, and affixed to the first elongated fabric member with the second side of the second elongate fabric member proximate the first side of the first elongate fabric member, wherein an area of the second elongate fabric member, which overlays the first elongate fabric member, defines a tourniquet portion of the first elongate fabric member;
a third elongate fabric member having a length, a first side, an opposing second side, a first end, and an opposing second end, wherein the third elongate fabric member is secured to the first elongate fabric member with the second side of the third elongate fabric member proximate the first side of the first elongate fabric member and a second end of the third elongate fabric member proximate the tourniquet portion, wherein the first end of the third elongate fabric member extends distal the tourniquet portion and secures to the first elongate fabric member along the lengths of the third elongate fabric member and the first elongate fabric member and the first end of the third elongate fabric member to form a first pocket having a first pocket opening proximate the tourniquet portion of the first elongate fabric member,
a fourth elongate fabric member having a length, a first side, an opposing second side, a first end, and an opposing second end, wherein the fourth elongate fabric member is secured to the first elongate fabric member with the second side of the fourth elongate fabric member proximate the first side of the first elongate fabric member and a second end of the fourth elongate fabric member proximate the tourniquet portion, wherein the first end of the fourth elongate fabric member extends distal the tourniquet portion and secures to the first elongate fabric member along the lengths of the fourth elongate fabric member and the first elongate fabric member and the first end of the fourth elongate fabric member to form a second pocket having a second pocket opening proximate the tourniquet portion of the first elongate fabric member;
a fifth elongate fabric member carried within the first pocket, extending through the first pocket opening, across the tourniquet portion, through the second pocket opening, and carried within the second pocket;
a windlass carried by the fifth elongate fabric member along the tourniquet portion; and
a first retaining member adjustably secured to the third elongate fabric member, adapted to capture a first end of the windlass and positionable to change a distance between the retaining member and the windlass.

20. A tourniquet belt comprising:
a first elongate fabric member having a first stiffness, a length, a first side, an opposing second side, a first end, and an opposing second end;
a second elongate fabric member having a first side, an opposing second side, a second stiffness greater than the first stiffness, and affixed to the first elongated fabric member with the second side of the second elongate fabric member proximate the first side of the first elongate fabric member, wherein an area of the second elongate fabric member, which overlays the first elongate fabric member, defines a tourniquet portion of the first elongate fabric member;

a third elongate fabric member having a length, a first side, an opposing second side, a first end, and an opposing second end, wherein the third elongate fabric member is secured to the first elongate fabric member with the second side of the third elongate fabric member proximate the first side of the first elongate fabric member and a second end of the third elongate fabric member proximate the tourniquet portion, wherein the first end of the third elongate fabric member extends distal the tourniquet portion and secures to the first elongate fabric member along the lengths of the third elongate fabric member and the first elongate fabric member and the first end of the third elongate fabric member to form a first pocket having a first pocket opening proximate the tourniquet portion of the first elongate fabric member;

a fourth elongate fabric member having a length, a first side, an opposing second side, a first end, and an opposing second end, wherein the fourth elongate fabric member is secured to the first elongate fabric member with the second side of the fourth elongate fabric member proximate the first side of the first elongate fabric member and a second end of the fourth elongate fabric member proximate the tourniquet portion, wherein the first end of the fourth elongate fabric member extends distal the tourniquet portion and secures to the first elongate fabric member along the lengths of the fourth elongate fabric member and the first elongate fabric member and the first end of the fourth elongate fabric member to form a second pocket having a second pocket opening proximate the tourniquet portion of the first elongate fabric member;

a fifth elongate fabric member carried within the first pocket, extending through the first pocket opening, across the tourniquet portion, through the second pocket opening, and carried within the second pocket;

an adjustable slide buckle secured to the first end of the first elongate fabric member;

a windlass carried by the fifth elongate fabric member along the tourniquet portion, wherein the windlass comprises:
 a retaining notch on a first end of the windlass,
 a first aperture adapted to receive the fifth elongate fabric member, and
 a second aperture adapted to receive the fifth elongate fabric member;

a plurality of attachment points at which the fifth elongate fabric member is secured to the fourth elongate fabric member and first elongate fabric member;

a first retaining member secured to the third elongate fabric member and adapted to capture a first end of the windlass;

a first securing fabric member having a first end secured to the third elongate fabric member proximate the tourniquet portion and an opposing second end secured to the third elongate fabric member with the first retaining member carried on the first securing fabric member between the first and second end of the first securing fabric;

a first covering fabric member having a first end secured to the second end of the first securing fabric wherein a length of the first covering fabric is adapted to removably secure to a length of the first securing fabric capturing the first retaining member therebetween;

a second retaining member secured to the fourth elongate fabric member and adapted to capture a second end of the windlass;

a second securing fabric member having a first end secured to the fourth elongate fabric member proximate the tourniquet portion and an opposing second end secured to the fourth elongate fabric member with the second retaining member carried on the second securing fabric member between the first and second end of the second securing fabric; and a second covering fabric member having a first end secured to the second end of the second securing fabric wherein a length of the second covering fabric is adapted to removably secure to a length of the second securing fabric capturing the second retaining member therebetween;

wherein the retaining notch is adapted to receive a portion of at least one retaining member;

wherein a first end of the windlass is carried in the first pocket and a second end of the windlass is carried in the second pocket;

wherein a surface of the windlass, proximate the first surface of the second elongate fabric member, is arcuate;

wherein a distance between a first hem of the third elongate fabric member and a first hem of the fourth elongate fabric member is greater than a length of the windlass; and wherein a ratio of a length of the windlass to a distance between the first pocket opening and the second pocket opening is 1.3.

* * * * *